(12) United States Patent
Reid et al.

(10) Patent No.: US 7,357,851 B2
(45) Date of Patent: Apr. 15, 2008

(54) ELECTROCHEMICAL CELL

(75) Inventors: Terence Alan Reid, Abingdon (GB); Shridhara Alva Karinka, Chelmsford, MA (US); Milind P. Nagale, Lowell, MA (US); Yi Wang, Southborough, MA (US); Gurdial Sanghera, Oxon (GB)

(73) Assignee: Abbott Laboratories, Abbott Park, IL (US)

( * ) Notice: Subject to any disclaimer, the term of this patent is extended or adjusted under 35 U.S.C. 154(b) by 61 days.

(21) Appl. No.: 10/674,955

(22) Filed: Sep. 30, 2003

(65) Prior Publication Data

US 2005/0067280 A1   Mar. 31, 2005

(51) Int. Cl.
*G01N 27/327* (2006.01)

(52) U.S. Cl. ............... 204/403.04; 204/403.1; 204/403.14

(58) Field of Classification Search .................. 204/403.4–403.14, 416–418, 400, 424, 409–412
See application file for complete search history.

(56) References Cited

U.S. PATENT DOCUMENTS

| | | | |
|---|---|---|---|
| 5,045,828 A | 9/1991 | Kulwicki et al. | |
| 5,185,256 A | 2/1993 | Nankai et al. | |
| 5,229,282 A | 7/1993 | Yoshioka et al. | |
| 5,509,410 A | 4/1996 | Hill et al. | |
| 5,677,538 A | 10/1997 | Moustakas et al. | |

| | | | |
|---|---|---|---|
| 2003/0015422 A1 * | 1/2003 | Fritsch et al. ............ 204/403.01 |

FOREIGN PATENT DOCUMENTS

| | | |
|---|---|---|
| EP | 0 390 390 | 10/1990 |
| WO | WO 90/12314 A1 * | 10/1990 |
| WO | 02/054055 | 7/2002 |
| WO | 03/005639 | 1/2003 |
| WO | 03/032411 A2 | 4/2003 |
| WO | 03/056319 | 7/2003 |

OTHER PUBLICATIONS

Englsih language translation of WO 90/12314 A1, patent published Oct. 18, 1990.*
International Search Report, Feb. 28, 2005.

* cited by examiner

*Primary Examiner*—Alex Noguerola
(74) *Attorney, Agent, or Firm*—Merchant & Gould P.C.

(57) ABSTRACT

An electrochemical cell for detection and quantification of analytes in a liquid sample, particularly a liquid sample having a small volume. In a preferred embodiment, the electrochemical cell comprises an assembly of conducting layers and insulating layers. The electrochemical cell can be formed by depositing conducting materials and insulating materials in alternating layers on an insulating substrate. It is preferred that the layer furthest from the insulating substrate be an insulating layer to minimize the damage of the conducting layers during handling of the electrochemical cell. In another embodiment, the assembly of conducting layers and insulating layers can be formed on both major surfaces of the insulating substrate. The assembly can comprise at least one working electrode and at least one other electrode, e.g., a dual-purpose reference/counter electrode.

18 Claims, 4 Drawing Sheets

ELECTROCHEMICAL CELL

BACKGROUND OF THE INVENTION

1. Field of the Invention

This invention relates to electrochemical cells. More specifically, the invention relates to electrochemical cells suitable for the detection and measurement of concentration of analytes in liquid samples.

2. Discussion of the Art

For conventional electrochemical analysis of a liquid sample, electrodes are dipped in the sample for electrochemical determination of the type of analyte or measurement of the concentration of analyte or both. The electrodes are spaced apart from each other, and the electrolytes in the sample provide ionic communication between the electrodes. In a majority of situations, the sample is static during measurement; in some instances, the sample flows through an electrochemical detector when the sample is in a fluid motion, such as in the case of flow injection analysis. The dimensions of the electrodes define the volume of the sample required for the measurement. The constraints relating to the volume of the sample and the requirement of rapid measurement may call for the use of microelectrodes, when the volume of the sample is not sufficient to cover the surface area of electrodes of conventional size.

Different methods of forming microelectrodes for the fabrication of electrochemical cells have been demonstrated. Interdigitated electrodes or band electrodes can be formed, with the electrodes being in close proximity to minimize the volume of sample required to perform an electrochemical measurement. In these devices, the electrodes are positioned on the same surface. U.S. Pat. No. 5,045,828 describes a humidity sensor comprising (a) a substrate having an electrically insulating surface; (b) a pair of spaced electrodes on the surface; and (c) a film having a thickness of approximately 5 microns or less on the surface interconnecting the electrodes. Conventional biosensors have a working electrode and a dual-purpose reference/counter electrode on the same major surface of an insulating substrate. The reactive chemistry is positioned on either the working electrode or on both the dual-purpose reference/counter electrode and the working electrode. U.S. Pat. No. 5,509,410 describes a sensor system adapted for releasable attachment to signal readout circuitry. The strip comprises an elongated support adapted for releasable attachment to readout circuitry; a first conductor and a second conductor each extending along the support and comprising means for connection to the circuitry. An active electrode, positioned to contact a liquid mixture and the first conductor, comprises a deposit of an enzyme capable of catalyzing a reaction involving the compound and preferably an electron mediator, capable of transferring electrons between the enzyme-catalyzed reaction and the first conductor. A reference electrode is positioned to contact the mixture and the second conductor. The system includes circuitry adapted to provide an electrical signal representative of the current.

WO 03/05639 discloses a microelectrode in the form of a receptacle. The receptacle comprises a working electrode in the wall of the receptacle, typically having a small surface area. A counter electrode is also present, the electrode typically having a much larger surface area than that of the working electrode, generally a surface area which is at least an order of magnitude larger than that of the working electrode. The electro-active substance may be placed into the receptacle and is optionally dried into position. The sample is then applied to the receptacle in order that testing can be carried out. The electro-active substance will typically not contact the working electrode in the wall of the receptacle during storage and therefore fouling of this electrode is minimized.

Various references in the prior art describe methods of fabrication of electrochemical cells for various analytical applications. Some of these references describe electrochemical cells having electrodes positioned side-by-side and having reagents on the surfaces of the electrodes, while other of the references describe electrochemical cells having a receptacle having one of the electrodes along the wall of an electrochemical cell and reagents positioned away from the active electrode. The positions and dimensions of the electrodes constituting the cell determine the volume of the electrochemical cell. Therefore, it would be desirable to provide electrochemical cells where the electrodes are positioned in such a manner as to decrease the volume of liquid sample required by the cell, in which positioning of reagents can be in contact with the working electrode.

SUMMARY OF THE INVENTION

This invention provides an electrochemical cell for detection and quantification of analytes in a liquid sample, particularly a liquid sample having a small volume.

In a preferred embodiment, the electrochemical cell comprises an assembly of conducting layers and insulating layers. The electrochemical cell can be formed by depositing conducting materials and insulating materials in alternating layers on an insulating substrate. It is preferred that the layer furthest from the insulating substrate be an insulating layer to minimize the damage of the conducting layers during handling of the electrochemical cell. A passage can be formed through the conducting layers and the insulating layers, either including or not including the insulating substrate, to expose the edges of the layers, which collectively form the wall or walls of the passage. The exposed edges of the conducting layers form the electrodes of the electrochemical cell. The electrochemical cell comprises at least one working electrode and at least one other electrode, e.g., a dual-purpose reference/counter electrode. Alternatively, the electrochemical cell can comprise at least one working electrode, one reference electrode, and one counter electrode. The shape and the dimensions of the passage can be selected to optimize the area of the exposed electrodes and the volume of the electrochemical cell. As used herein, the term "optimize" refers to the process of maximizing the surface area of the electrodes, while minimizing the volume of the liquid sample, so as to obtain an accurate electrical response with a very small liquid sample.

In another embodiment, the assembly of conducting layers and insulating layers can be formed on both major surfaces of the insulating substrate. The assembly can comprise at least one working electrode and at least one other electrode, e.g., a dual-purpose reference/counter electrode. Alternatively, the electrochemical cell can comprise at least one working electrode, one reference electrode, and one counter electrode. It is preferred that the electrochemical cell have insulating layers overlying the major surfaces of the conducting layers not facing the insulating substrate to minimize the damage of the conducting layers during handling of the electrochemical cell.

The number of conducting layers in the assembly determines the number of electrodes in the electrochemical cell. The conducting layers functioning as working electrodes preferably contain reagent(s) specific to one or more analytes in the liquid sample or support a reagent-containing layer containing reagent(s) specific to one or more analytes in the liquid sample, such as, for example, glucose, ketone bodies, lactate etc. One or more of these conducting layers can also be used to determine the interference from electroactive species that may be present in the sample. At least one of these conducting layers must carry out the function of a reference electrode. Optionally, the electrochemical cell can contain a counter electrode, separate and distinct from a reference electrode.

The volume of liquid sample(s) that can be introduced into the electrochemical cell is determined by the cumulative thickness of the individual layers and the perimeter of the passage(s). More than one passage can be formed in the electrochemical cell to provide a plurality of electrochemical cells in an assembly of conducting layers and insulating layers. In these situations, all the passages can be used to perform a plurality of identical assays for the same set of analytes with a single liquid sample to increase the sensitivity of the assay, or all the passages can be used to perform a plurality of identical assays for the same set of analytes, but with different liquid samples. A plurality of passages can also be used for the analyses of different analytes with a single liquid sample. The locations of the passages can operate to either minimize the volume of sample or to minimize cross talk, depending on the application.

The invention also provides a method for constructing electrochemical cells that can operate with small volumes of sample. The electrochemical cell of this invention can be constructed by interlaying conducting layers and insulating layers and then forming a passage to expose the edges of the layers to a liquid sample. The conducting layers exposed to the liquid sample form the electrodes of an electrochemical cell. In the passage, adjacent conducting layers, i.e., electrodes, are separated by an insulating layer. Specificity to the electrochemical cell can be provided by incorporating a reagent that specifically reacts with an analyte of interest, thereby generating a measurable signal.

The reagents specific for an analyte can be applied at the same time as the layer of conducting material in the form of a discrete layer, wherein the appropriate reagent(s) is (are) present in a layer of conductive material forming an electrode; alternatively, the reagent(s) can be applied as a layer impregnated with reagent(s), the applied layer being separate from the layer forming the electrode; as a further alternative, the reagent(s) can be coated along the wall or walls of a passage.

The electrochemical cells of this invention can be used for any type of electrochemical measurement. The conducting layers can be modified to measure a specific analyte. The electrochemical cell can utilize ion sensitive electrodes. In addition, the electrochemical cell can be an electrochemical biosensor having the appropriate reagent(s) in a conducting layer that is specific to an analyte of interest.

This invention makes it possible to prepare electrochemical cells that require extremely low volumes of sample. The electrochemical cells of this invention can be reproduced with great accuracy and precision. Assays for a single analyte or a plurality of analytes can be performed with the electrochemical cell of this invention.

DETAILED DESCRIPTION

Figure 1:
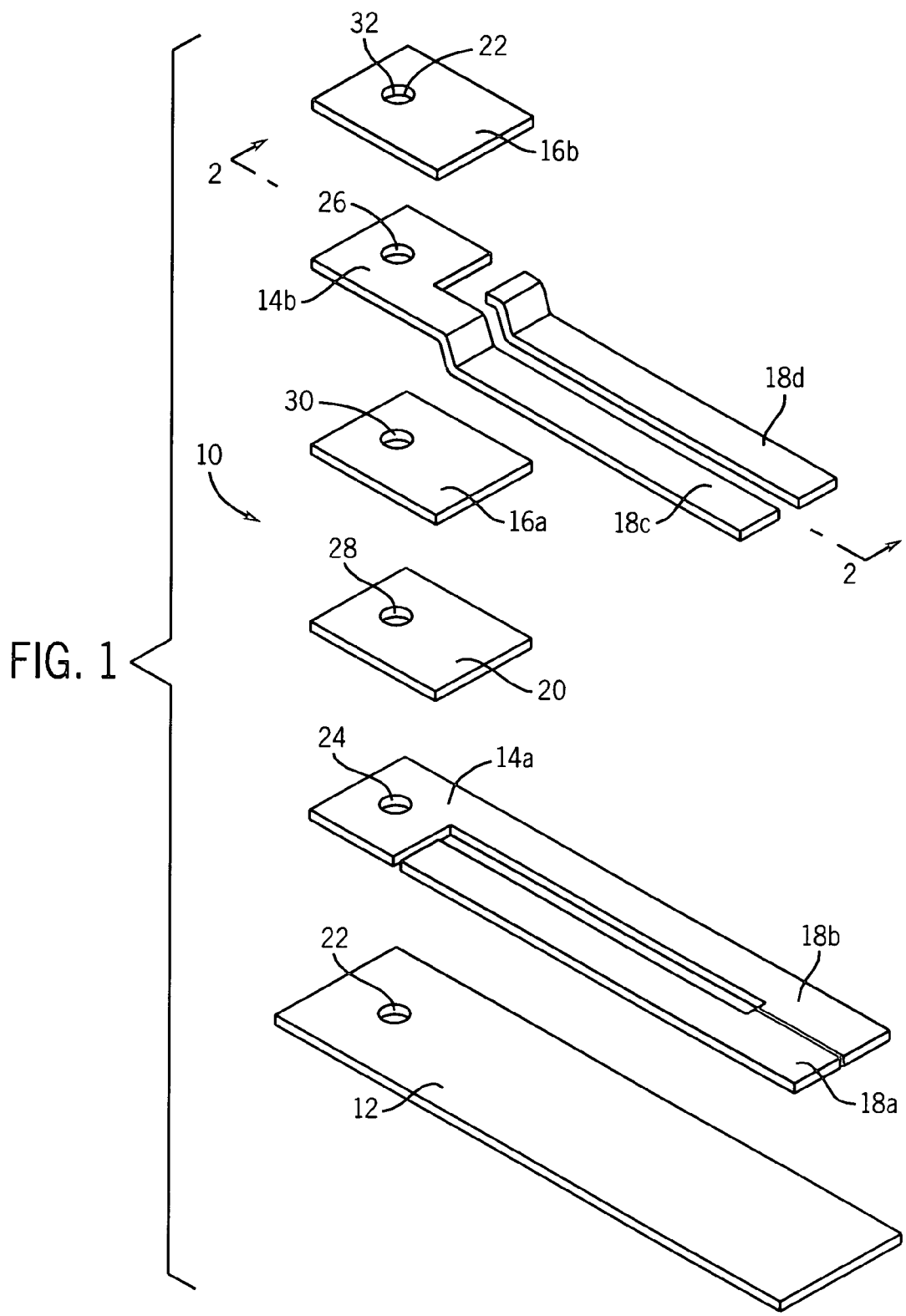
FIG. 1 is an exploded perspective view of one embodiment of the electrochemical cell of this invention.

As used herein, the expression "electrochemical cell" refers to a device comprising a working electrode and a counter electrode which are connected to one another electrically. When in use, electrochemical reactions occurring at each of the electrodes cause electrons to flow to and from the electrodes, thus generating a current. An electrochemical cell can be set up either to harness the electrical current produced, for example in the form of a battery, or to detect electrochemical reactions which are induced by an applied current or voltage.

As used herein, the term "layer" means a single thickness, coating, or stratum that covers a surface. The expression "major surface" means the surface of a substrate that has a larger area than another surface. A planar substrate will have two major surfaces and at least one minor surface. The term "passage" means a path, channel, or duct through which a liquid can pass. In the invention described herein, a passage can run through all the layers, including the substrate, or can run through less than all of the layers. The term "volume" means the volume of a liquid required to fill a single passage or a plurality of passages. An electrochemical cell can have a single passage or a plurality of passages. The term "aperture" means an opening into which a liquid sample can enter the passage or a segment of the passage. The passage has a depth and the aperture has an area.

The expression "working electrode" means an electrode where the reaction of interest takes place. The current is proportional to the concentration of an analyte, e.g., glucose, at the working electrode; the expression "reference electrode" refers to an electrode that measures the potential at the interface of the working electrode and the sample as accurately as possible; the expression "counter electrode" refers to an electrode that ensures that the correct potential difference between the reference electrode and the working electrode is being applied; a "dual-purpose reference/counter electrode" is an electrode that acts as a reference electrode as well as a counter electrode. In an ideal situation, no current passes through the reference electrode. The potential difference between the working electrode and the reference electrode is assumed to be the same as the desired potential at the working electrode. If the potential measured at the working electrode is not the potential desired at the working electrode, the potential that is applied between the counter electrode and the working electrode is altered accordingly, i.e., the potential is either increased or decreased. The reaction at the counter electrode is also equal and opposite to the charge transfer reaction occurring at the working electrode, i.e., if an oxidation reaction is occurring at the working electrode then a reduction reaction will take place at the counter electrode, thereby allowing the sample to remain electrically neutral. No current passes through an ideal reference electrode, and such an electrode maintains a steady potential; current does pass through a dual-purpose reference/counter electrode, and thus, the dual-purpose reference/counter electrode does not maintain a steady potential during the measurement. At low currents and/or at short durations of time for measurement, the shift in potential is small enough such that the response at the working electrode is not significantly affected, and hence the dual-purpose reference/counter electrode is designated a dual-purpose reference/counter electrode.

The expression "conducting layer" means the electrically conducting layer that is interposed between two insulating layers. The expression "insulating layer" means either a layer that is interposed between two conducting layers or a layer that overlies a conducting layer, one major surface of the insulating layer being in contact with one major surface of the conducting layer. The resistance of the insulating layer is sufficiently high that current does not flow through the insulating layer.

The term "reagent(s)" means substance(s) that is (are) an active component(s) of the detection and quantification process, whereby the presence or concentration of an analyte in a sample is determined. Reagents include, but are not limited to, enzymes, mediators, co-enzymes, ionophores, cells, or combinations of the foregoing. The reagents typically comprise an enzyme and a mediator. A mediator is a chemical species that has two or more oxidation states of distinct electro-active potentials that allow a reversible mechanism of transferring electrons/charge to an electrode. The enzyme reacts with the analyte in the sample, thereby catalyzing oxidation of the analyte. The enzyme is reduced in the oxidation reaction, and the reduced enzyme is regenerated by the mediator. Representative examples of enzymes include glucose oxidase, lactate oxidase, beta hydroxybutyrate dehydrogenase, and the like. Representative examples of mediators include ferrocene, ferricyanide, quinones, and the like. Alternatively, ionic species and metal ions can be used in place of the enzyme to form electrochemically detectable compounds when they react with the analyte, such as ionophores used for the ion-sensitive electrodes.

Figure 2:
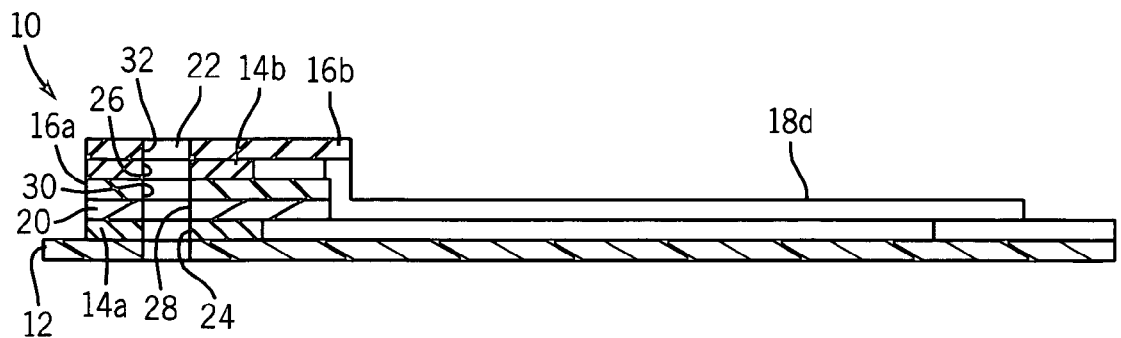
FIG. 2 is a side view in elevation of a section taken along line 2-2 of the electrochemical cell of FIG. 1.
Figure 3:
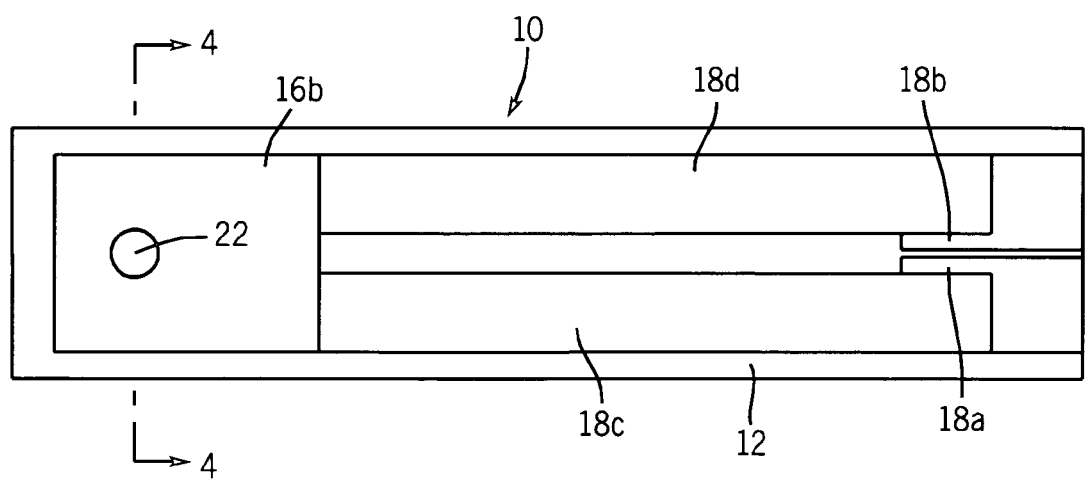
FIG. 3 is an end view in elevation of a section taken along line 3-3 of the electrochemical cell of FIG. 2.
Figure 4:
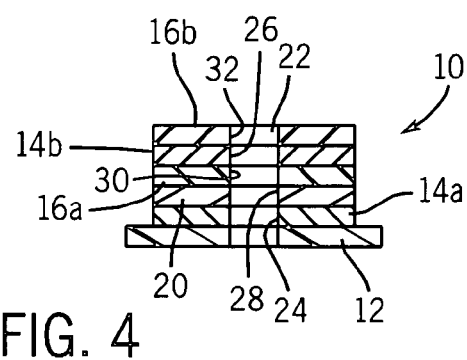
FIG. 4 is a top plan view of an electrochemical cell of FIG. 1.

Referring now to FIGS. 1-4, an electrochemical cell 10 comprises an insulating substrate 12, a plurality of conducting layers 14a, 14b, and an insulating layer 16a interposed between the two conducting layers 14a and 14b. Another insulating layer 16b overlies the conducting layer furthest from the insulating substrate 12. Conductive tracks 18a, 18b are applied to the insulating substrate 12, and conductive tracks 18c, 18d are applied over the conductive tracks 18a, 18b, respectively. A layer of reagent(s) 20 overlies the conducting layer 14a. A passage 22 passes through (a) the insulating substrate 12, (b) the plurality of conducting layers 14a, 14b, (c) the plurality of insulating layers 16a, 16b, and (d) the layer of reagent(s) 20. The edges 24, 26 of the conducting layers 14a, 14b, respectively, the edge 28 of the layer of reagent(s) 20, and the edges 30, 32 of the insulating layers 16a, 16b, respectively, form the wall of the passage 22. The conducting layers 14a, 14b form the electrodes of the electrochemical cell 10. In the embodiment shown in FIGS. 1-4, there are two insulating layers 16a, 16b, and two conducting layers 14a, 14b in addition to the insulating substrate 12.

Figure 5:
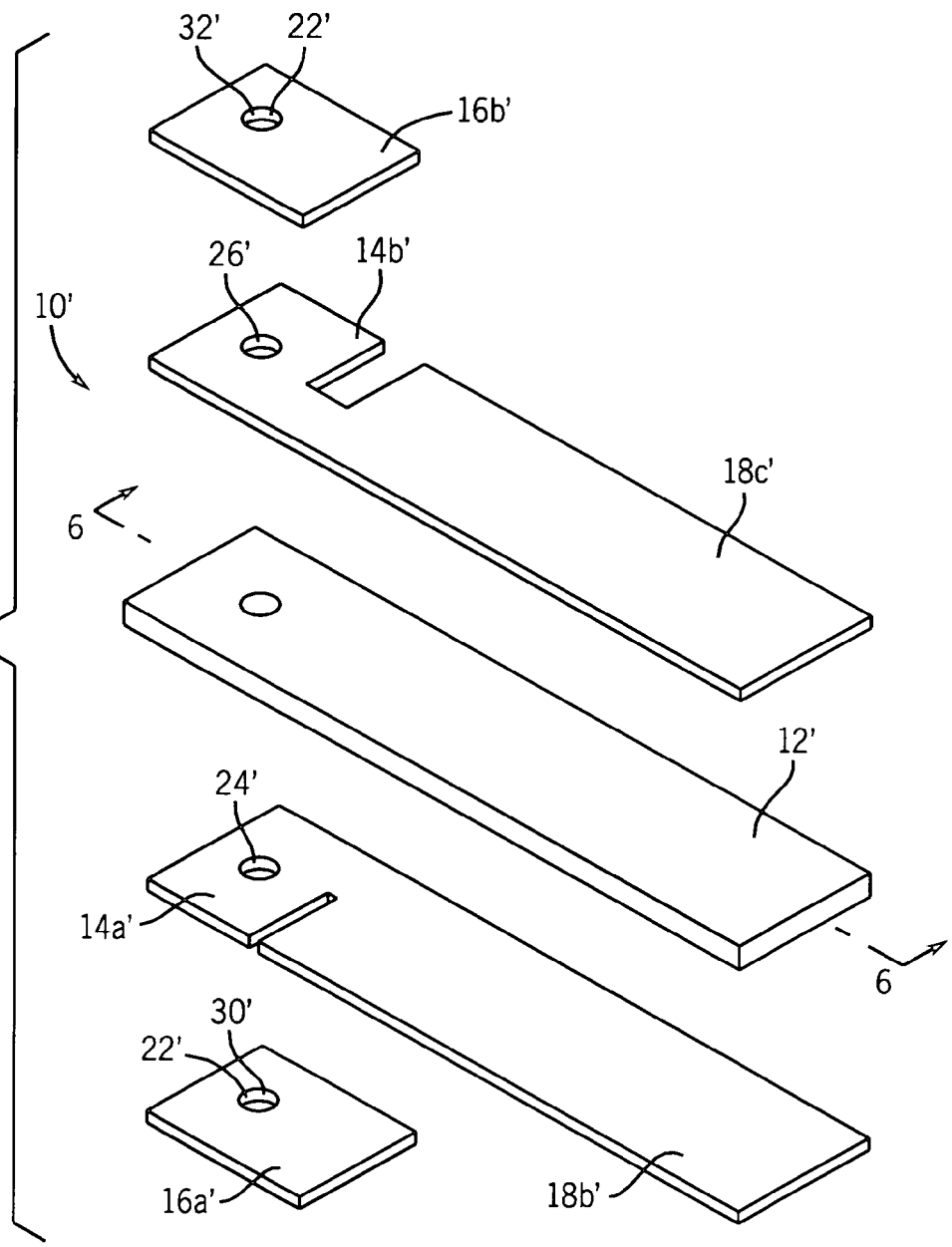
FIG. 5 is an exploded perspective view of one embodiment of the electrochemical cell of this invention.
Figure 6:
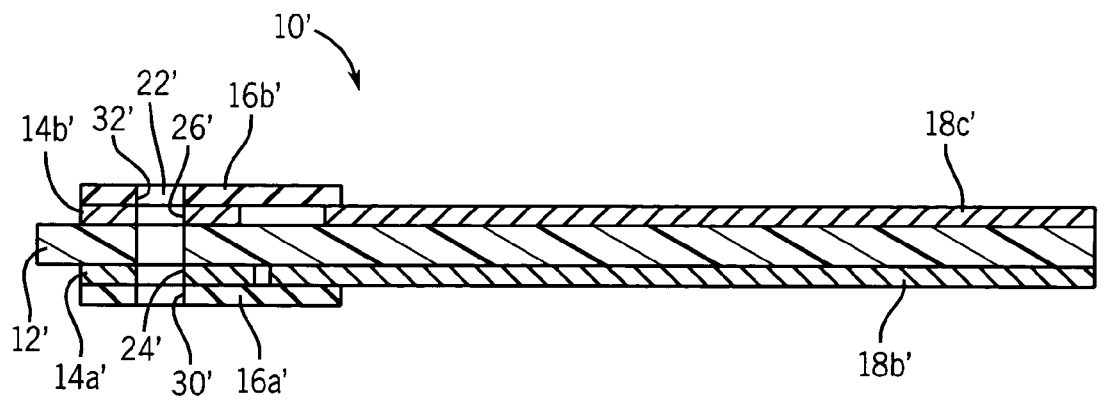
FIG. 6 is a side view in elevation of a section taken along line 6-6 of the electrochemical cell of FIG. 5.
Figure 7:
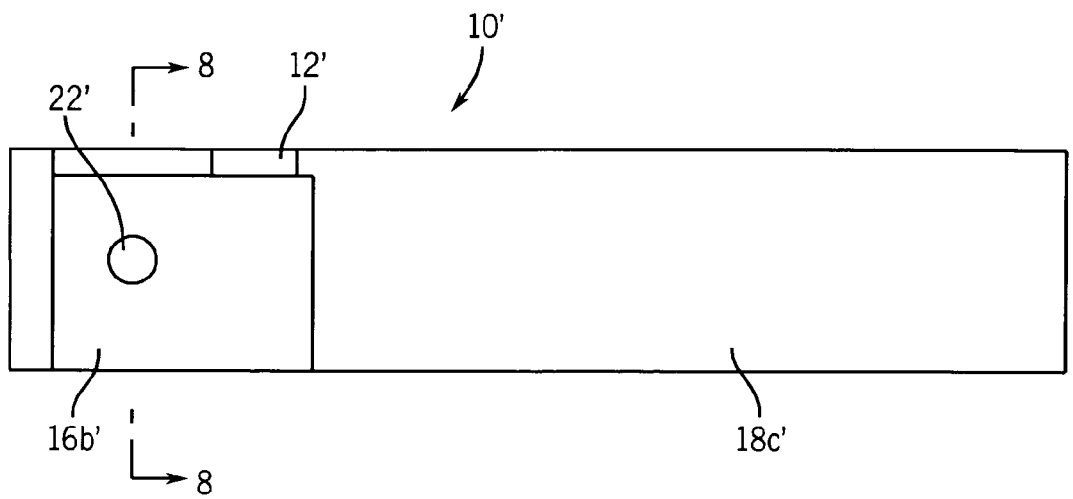
FIG. 7 is an end view in elevation of a section taken along line 7-7 of the electrochemical cell of FIG. 6.
Figure 8:
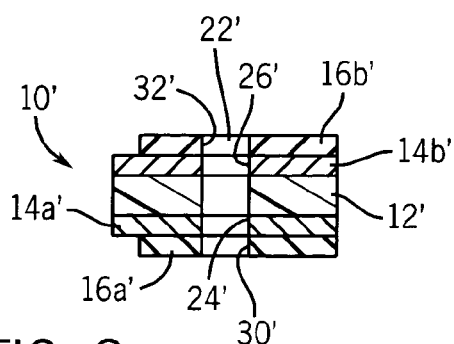
FIG. 8 is a top plan view of an electrochemical cell of FIG. 5.

Referring now to FIGS. 5-8, an electrochemical cell 10' comprises an insulating substrate 12', a plurality of conducting layers 14a', 14b', and a plurality of insulating layers 16a', 16b', the insulating substrate 12' interposed between the two conducting layers 14a', 14b'. The insulating layers 16a', 16b' overlie the conducting layers 14a', 14b', respectively. Conductive track 18b' is applied to one major surface of the insulating substrate 12', and conductive track 18c' to another major surface of the insulating substrate 12'. A passage 22' passes through the insulating substrate 12', the plurality of conducting layers 14a', 14b', and the plurality of insulating layers 16a', 16b'. The edges 24', 26' of the conducting layers 14a', 14b', respectively, and the edges 28', 30' of the insulating layers 16a', 16b', respectively, form the wall of the passage 22'. The conducting layers 14a', 14b' form the electrodes of the electrochemical cell 10'. In the embodiment shown in FIGS. 5-8, there are two insulating layers 16a', 16b' and two conducting layers 14a', 14b' in addition to the insulating substrate 12'. It is preferred that the conducting layer 14a' contain at least one reagent suitable for an assay for determining the presence or concentration of an analyte of interest. A reagent-containing layer (not shown) separate from the conducting layer 14a' can be placed so as to be in face-to-face contact with the conducting layer 14a' to supply any reagent(s) not present in the conducting layer 14a', if the conducting layer 14a' does not contain all of the reagent(s) needed to carry out the assay.

Materials that are suitable for the insulating substrate include, but are not limited to, polymeric materials, such as, for example, polyvinyl chloride, polycarbonate, polyester, and the like. These materials are commercially available. The purpose of the insulating substrate is to provide mechanical support for the layers overlying the substrate.

Materials that are suitable for the conducting layers are electrically conductive and include, but are not limited to, carbon, metals, such as, for example, gold, palladium, platinum, copper, silver, electrically conductive compounds, such as, for example, silver chloride, and semi-conducting materials, such as, for example, indium doped tin oxide. In some instances, more than one conductive material can be mixed to form a conducting layer; in other instances, a conducting layer can be prepared by overlying one conducting material with another conducting material.

The conducting layer can be formed by depositing an electrically conductive material on an insulating layer by means of conventional techniques, such as, for example, screen printing, vapor deposition, ink jet printing, etc.

The electrochemical cell can also contain at least one additional conducting layer and an insulating layer for each additional conducting layer. One of the additional conducting layers can form a counter electrode. As stated previously, additional conducting layers can function as working electrodes. These additional conducting layers functioning as working electrodes allow different measurements to be carried out on the same sample by applying different potentials across two or more of the conducting layers functioning as working electrode/counter electrode pairs. Alternatively, the same potential may be applied to each conducting layer functioning as a working electrode and the same measurement recorded several times for the same sample. This procedure helps to eliminate or detect errors in the measurements taken.

Additional working electrodes can be employed in the electrochemical cell for one or more of the following functions:

1) As a second working electrode to determine the same analyte as the first working electrode by increasing the surface area of the working electrode;
2) As a second working electrode to determine the same analyte as the first working electrode, whereby the integrity of the measurement (as a counter check on the first measurement) is verified;

3) As a second biosensor for an analyte to measure a second analyte, different from the first analyte, in the liquid sample;
4) As a means for measuring the background signal to compensate for the interfering agents in the liquid sample.

The additional working electrode can use the same dual-purpose reference/counter electrode as the first electrode or can have its own dual-purpose reference/counter electrode.

The insulating layer provides a separation between two conducting layers to prevent short circuits. The material for the insulating layer is typically a polymer, such as, for example, an acrylate, polyurethane, polyolefin, polyester, e.g., polyethylene terephthalate, or the like. Polycarbonate and other plastics and ceramics are also suitable as materials for the insulating layer. The insulating layer can be formed by evaporating a solvent from a solution of the polymer. Liquids that harden after application can also be used, e.g., varnishes. Alternatively, cross-linkable polymer solutions can be used. These can be cross-linked by exposure to heat or electromagnetic radiation or by mixing together the active parts of a two-component cross-linkable system. Dielectric inks can also be used to form insulating layers. A preferred material for the insulating layers is commercially available under the trademark "POLYPLAST" (Sericol Ltd., Broadstairs, Kent, UK). The insulating layer can be deposited over a given area of the conducting layer in such a manner to leave a portion of the conducting layer exposed in order to provide electrical contacts so that the electrochemical cell can be connected to an apparatus for measuring the electrochemical response, such as voltage difference (in mV) or current (in amperes). The insulating layer can be deposited by any method in the art, such as, for example, screen-printing, laminating, or other conventional chemical depositing techniques. A preferred insulating layer can be formed by using a preformed polymeric suspension, such as one designated by the trademark Sericard® (Sericol Ltd., Broadstairs, Kent, UK), or a monomeric solution that is polymerized after being applied.

At least two conducting layers are required, one in order to function as the working electrode and another in order to function as the reference electrode of the electrochemical cell. If only two conducting layers are used, one conducting layer can function as the working electrode and the other conducting layer can function as a dual-purpose reference/counter electrode. The electrochemical cell can contain a third conducting layer, which will function as the counter electrode. A plurality of working electrodes can be defined by utilizing additional conducting layers. These working electrodes can be used for the measurement of the presence or the amount or both the presence and the amount of a single analyte or of a plurality of analytes in a given sample.

A conducting layer that functions as a working electrode is preferably formed from carbon, palladium, gold, or platinum, for example, in the form of conductive ink. The conductive ink may contain additional materials, such as, for example, platinum, or graphite, or both platinum and graphite. Two or more layers may be used to form a working electrode, the layers being formed of the same or different materials.

A conducting layer that functions as the dual-purpose reference/counter electrode, reference electrode, or counter electrode is preferably formed from carbon, palladium, gold, or platinum, Ag/AgCl, for example, in the form of conductive ink. The conductive ink may contain additional materials, such as, for example, platinum or graphite or both. Two or more layers may be used to form the dual-purpose reference/counter electrode, the layers being formed of the same or different materials. In the case where three conducting layers are employed, one of the conducting layers can function as a working electrode, one of the conducting layers can function as a reference electrode, and one of the conducting layers can function as a counter electrode.

The number of conducting layers in the electrochemical cell determines the number of electrodes in the electrochemical cell. These conducting layers preferably contain reagent(s) specific to one or more analytes in the sample, such as, for example, glucose, ketone bodies, lactate etc., or are adjacent to a layer containing reagent(s) specific to one or more analytes in the sample, such as, for example, glucose, ketone bodies, lactate etc. One or more of these conducting layers can also be used to determine interference from electroactive species that may be present in the sample. At least one of these conducting layers must function as reference electrode. Optionally, the electrochemical cell can also contain a conducting layer that functions as a counter electrode.

In the method of this invention, the liquid sample can be a sample of whole blood. In other electrochemical cells suggesting the use of three electrodes, the liquid sample can be whole blood that has been filtered or treated to remove red blood cells or other hemocytes.

There are numerous ways to prepare the electrochemical cell of this invention. In one embodiment, an insulating support is coated with a conducting material, such as carbon or conductive metal, by means of screen-printing or other deposition technique, such as sputtering, to form a first conducting layer. The reagent(s) is (are) then applied over the conducting layer by any method of application, such as, for example, drop coating, screen-printing, ink jet printing, or chemical attachment of the reagent to the layer of conducting material, such as, for example, by means of a chemical linking group. One can also apply the reagent(s) by in situ polymerization of monomers, such as, for example, pyrrole or acrylamide, in the presence of reactive components, such as, for example, enzyme or mediator, thereby resulting in the physical entrapment of the reactive component in a polymeric matrix. The reagent(s) is (are) located in the region of the electrochemical cell through which the passage is to be formed. The area of the reagent layer is greater than the area of the aperture of the passage. An insulating layer is then deposited over the first conducting layer and reagent layer in such a manner that a part of the first conducting layer is exposed to enable removable contact with a measurement device. A second conducting layer is then applied over the insulating layer in such a manner as to leave the contact area of the second conducting layer, i.e., the dual-purpose reference/counter electrode, exposed. An insulating layer is applied over the second conducting layer in such a manner as to leave the contacts exposed. A passage is then formed by cutting through the insulating layers and the conducting layers and, if desired, through the insulating substrate.

The passage can be formed by cutting though the layers by any method, including but not limiting to, punching, die-cutting, milling, drilling, ablating, laser cutting, etc. One of ordinary skill in the art can readily choose an appropriate method, based on the physical properties of the layers and the expected use of the electrochemical cell. With respect to punching, a single passage can be punched from either the top of the electrochemical cell assembly or from the bottom of the electrochemical cell assembly. Overlapping double passages can be punched from either the top of the electrochemical cell assembly or from the bottom of the electrochemical cell assembly. Laser-cutting by means of ultraviolet radiation provides a higher yield than do other methods. Care should be taken to ensure that the mechanical pressure experienced by the layers during the formation of the passage does not result in electrical conductivity between two adjacent conducting layers. It is also envisioned that the physical step of forming the passage can be followed by a chemical etching process to create patterns that would enhance the surface area of the electrodes.

In an alternative embodiment, a layer containing a mixture of silver and silver chloride is printed on one major surface of an insulating substrate. The insulating substrate is preferably polyvinyl chloride (PVC), Melinex® polyester (E. I. duPont de Nemours, Inc.). This layer is covered with an insulating layer, but leaving a contact area for removable connection with the measurement device. The insulating layer is preferably made of Sericard® material. The other major surface of the insulating substrate is then coated with a first conducting layer. The first conducting layer preferably comprises carbon or a conductive metal. Coating is carried out by screen-printing or another technique, such as sputtering. The reagent(s) is (are) then printed over the first conducting layer by any deposition method, such as, for example, drop coating, screen printing, ink jet printing, etc., in the area where the passage is to be formed, such that dimension of the area where the reagent(s) is (are) deposited is greater than the dimension of the aperture of the passage. An insulating layer is then applied to cover the reagent layer and the first conducting layer, while allowing a contact area to be exposed for removable connection with the measurement device. A passage is then formed in such a manner that the passage passes through the insulating layers, insulating substrate, and the conducting layers, as well as the reagent.

The electrochemical cell of this invention can be prepared by a photopolymerization technique in which a photopolymerizable material is applied over a conducting layer and the portion of the photopolymerizable material to be retained in the final article is cured by means of the appropriate application of electromagnetic radiation. After the desired number of conducting layers and photopolymerizable layers are applied, the uncured portions of the photopolymerizable layers are removed by washing in an appropriate solvent.

The dimensional parameters of the layers are affected by the method of applying the layer to a substrate or to an adjacent layer. For example, screen-printing typically provides a thickness of from about 2 µm to about 100 µm, depending on the screen mesh and the physical properties of the material being applied. Sputtering typically provides a thickness of from about 10 nm to about 10 µm. Lamination can provide a thickness of from about 25 µm to about 6 mm. The insulating layers and the conducting layers must be made of material having sufficient rigidity to avoid being excessively compressed under mechanical forces, which excessive compression would result in variations in the thickness of the electrodes as well as increasing the possibility of bringing about short circuits.

Materials that can be used as reagents, either in a reagent-containing layer or incorporated into the material of a conducting layer functioning as a working electrode, include enzymes, such as glucose oxidase, glucose dehydrogenase, beta-hydroxybutyrate dehydrogenase, lactate dehydrogenase, etc., and a coenzyme, such as, for example, nicotinamide adenine dinucleotide (NAD), if required. The reagent-containing layer can further include an oxidation-reduction mediator.

The reagent(s) of the electrochemical cell need not be introduced to the electrochemical cell by way of a reagent layer. The reagent(s) can be applied along the wall of the passage after the passage is created. The reagent(s) can be provided in a porous material wherein the porous material is positioned so as to fill the cavity surrounded by the wall of the passage.

If used, the amount(s) of reagent(s) required in the electrochemical cell are not critical, and the precise amount(s) of reagent(s) to be used for desired performance can readily be determined by one of ordinary skill in the art.

A passage for receiving the liquid sample can be formed through the various layers of the electrochemical cell. The exposed edges of the conducting layers forming a portion of the wall of the passage define the electrodes of the electrochemical cell. The cross-section of the passage can have any shape, e.g., circular, elliptical, polygonal. The shapes can be regular, e.g., equilateral triangle, square, or irregular, e.g., polygon having sides of differing lengths. In addition, the shape of the cross-section of the passage can vary along the length of the passage. Furthermore, each layer can have an aperture of a different shape. It is preferred that the surface areas of the electrodes exposed to the passage be optimized to obtain the desired signal to noise ratio. In general, the higher the surface area, the better the signal to noise ratio. The passage preferably includes at least one opening to serve as a vent to enable the passage to be filled with liquid easily. The opening is preferably formed in the insulating substrate. If such an opening(s) is (are) not present, the sample may not enter the passage when it flows into the aperture, or it may enter the passage only with difficulty. The opening(s) can be smaller than the aperture, but should be large enough to allow air to escape from the electrochemical cell.

In some embodiments, a passage need not be formed. In this type of embodiment, an end of the electrochemical cell is placed in contact with the liquid sample. The end of the electrochemical cell that contacts the liquid sample is characterized by having the edges of the conducting layers exposed.

In assays where an electroactive species in a liquid sample is measured without the need for any reagent at all, the conducting layer constituting the working electrode need not have any reagent deposited thereon. As is well-known, electrochemical measurement is carried out by using a working electrode coupled to a reference electrode. The measurement can involve a change in the potential (potentiometry) or the generation of current (amperometry). The electrodes by themselves do not exhibit specificity to an analyte. The specificity can be imparted to the electrode by having an enzyme (in the case of biosensor) that reacts with only one of a plurality of analytes in a mixture of analytes or by employing a filtration technique that would selectively allow only one of a plurality of analytes in a mixture to pass through a filtration device. In electrochemical measurements of certain analytes, such as dopamine in the brain, the determination of interfering agents in a "dummy" electrode of a biosensor is one example wherein an electrochemical measurement is carried out without the use of any reagent on the surface of the working electrode. See, for example, U.S. Pat. No. 5,628,890.

OPERATION

Any method of introducing liquid samples to the electrochemical cell can be used. The dimensions of the passage suitable for uptake of sample by capillary attraction can be specified. Other methods, such as, for example, gravitational forces, chemically-aided wicking, or suction by means of vacuum, can be used. In certain applications, the passage can be filled with a porous material that will allow uptake of the sample by wicking.

The aperture(s) in the passage can be designed to allow the electrochemical cell to be integrated with a device for extracting liquid biological samples from a subject. For example, a mechanical device, such as a lancet, or an optical device, such as a laser, can be directed at the sample extraction site through the aperture(s) of the passage to create an artificial opening in a human body (skin). The liquid sample emerging from the artificial opening can then be transferred to the electrochemical cell either by an additional mechanical force, such as, for example, suction provided by vacuum, or by a naturally provided force, such as, for example, gravitation. A device that is suitable for integrating the electrochemical cell of this invention is described in U.S. Pat. No. 6,093,156, incorporated herein by reference.

The electrochemical cell can be used as a flow cell, with liquid traversing the length of the passage under convection, diffusion, or osmosis. Based on the dimensions of the aperture(s) of the passage, larger species from the sample can be excluded. Representative examples of larger species include, but are not limited to, cells, protein, and skin.

The volume of a given passage specifies the volume of liquid sample required by that passage of the electrochemical cell. The overall volume of a given passage is equal to the sum of the volumes of each section of that passage. The volume of liquid required to fill a given passage in the electrochemical cell is determined by the cumulative thickness of the individual layers and areas of the various sections of that passage. It is preferred that any given passage not have a volume exceeding 1 microliter.

More than one passage can be formed in an electrochemical cell to form, in effect, a plurality of electrochemical cells in the assembly. In these situations, a plurality of passages can be used in a plurality of identical assays with one liquid sample to increase the sensitivity of the assay; alternatively, a plurality of passages can be used to perform a plurality of identical assays for the same analyte with different liquid samples or to perform assays for a plurality of analytes with a single liquid sample. The locations of the passages can be specified to either minimize the volume of sample required or to minimize cross talk, depending on the application. As the passages are moved farther apart, crosstalk is reduced. As the passages are moved closer together, a lower volume of sample is required.

Measuring devices that are suitable for use in this invention include any commercially available analyte monitor that can accommodate an electrochemical cell having a working electrode and a dual-purpose reference/counter electrode. Alternatively, an analyte monitor that can accommodate an electrochemical cell having a working electrode, a reference electrode, and a counter electrode can be used. Such analyte monitors can be used to monitor analytes, such as, for example, glucose and ketone bodies. In general, such a monitor must have a power source in electrical connection with the working electrode, the reference electrode, and the counter electrode. The monitor must be capable of supplying an electrical potential difference between the working electrode and the reference electrode of a magnitude sufficient to cause the electrochemical oxidation of the reduced mediator. The monitor must be capable of supplying an electrical potential difference between the reference electrode and the counter electrode of a magnitude sufficient to facilitate the flow of electrons from the working electrode to the counter electrode. In addition, the monitor must be capable of measuring the current produced by the oxidation of the reduced mediator at the working electrode.

In a measurement employing the electrochemical cell of this invention, a constant voltage is applied at the working electrode and the current is measured as a function of time. This technique is known as chronoamperometry. The voltage applied should be equal or higher to the voltage required to oxidize the reduced mediator. Thus, the minimum voltage required therefore is a function of the mediator.

The sample is responsible for the solution resistance. The solution resistance inhibits the flow of electrons. The effect of solution resistance on the measurement is minimized by this invention. Arranging the electrodes close together obviously minimizes the effect of solution resistance because solution resistance is a function of the spacing between the electrodes. By allowing the current to flow through a different electrode, the effect of solution resistance on the working electrode can be minimized.

In an amperometric measurement, the current should decay with time according to the Cottrell equation.

$$i_t = \frac{nFAC_o D_o^{1/2}}{\pi^{1/2} t^{1/2}}$$

where
$i_t$=the current at time t
n=number of electrons
F=Faraday's constant
A=area of the electrode
$C_o$=bulk concentration of the electrochemically active species
$D_o$=diffusion coefficient of the electrochemically active species.

Therefore, $i_t t^{1/2}$ should be a constant.

In an amperometric measurement, a constant voltage is applied at the working electrode with respect to the reference electrode, and the current between the working and counter electrodes is measured. The response of the electrochemical cell has two components, catalytic (glucose response component) and Faradaic (solution resistance component). If the resistance of the solution is minimized, the response of the electrochemical cell at any given time will have substantially higher glucose response component, as compared with the solution resistance component. Therefore, one is able to obtain good correlation with the concentration of glucose from the response of the electrochemical cell even at assay times as short as one second. If the resistance of the solution is high, the voltage experienced at the working electrode will lag significantly from the voltage applied. This lag is significantly higher for a two-electrode system, as compared with a three-electrode system. In the case of two-electrode system, the value of iR between the working and the reference electrode is significantly higher than that in a three-electrode system. In a three-electrode system, no current flows between the working electrode and the reference electrode, and hence the voltage drop is lower. Therefore, once the charging current (Faradaic current) decays to a minimum (within two to three milliseconds), the current observed is all catalytic current. In a two-electrode system, the charging current is not diminished until the voltage at the working electrode attains a steady state (reaches the applied voltage). Thus, in a two-electrode system, there is a slow decay of the response profile.

The passage of the electrochemical cell can be filled with a liquid sample by any of numerous methods. Filling can be carried out by, for example, capillary attraction, chemically-aided wicking, or vacuum. Alternatively, the liquid sample can flow through the passage. The manner of filling the electrochemical cell depends on the application, such as single use of the sensor or continuous measurements in a flow injection analysis.

The advantages of the invention described herein include the ability to use small volumes of liquid samples, improved current distribution, and a plurality of working electrodes.

Benefits provided by the electrochemical cell of this invention include the capability of using low volumes of biological samples, the capability of filling the electrochemical cell by capillary attraction or gravitational action; the capability of excluding large species if the dimensions of the apertures of the passages are sufficiently small; the capability of carrying out a plurality of measurements, including measurement of different electroactive species. The electrochemical cell of this invention can be used in several ways, such as, for example, with a device for forming an opening in the skin by having a lancing device traversing the passage of the electrochemical cell when the cell is placed against the skin and allowing the electrochemical cell to be filled with a liquid sample when the liquid sample flows directly from the site of the opening thus formed. Alternatively, the electrochemical cell can be used in the manner of a flow cell, with liquid sample traversing the passage(s) under such fluid transfer techniques as convection, diffusion, or osmosis.

The following non-limiting examples further illustrate the electrochemical cell of this invention.

EXAMPLE 1

This example illustrates a multi-layer electrochemical cell for the determination of glucose. The conducting layers were formed on one major surface of an insulating substrate (polyvinyl chloride, approximately 450 micrometers thick). A conducting layer (carbon, approximately 15 µm thick) was deposited on a PVC substrate by means of screen-printing. The dimension of the individual cell after being trimmed was 5 mm wide and 40 mm long. However, in the actual case, a plurality of cells were prepared in one card and then cut into discrete cells having the dimensions described. The reagents, which consisted of glucose oxidase, ferrocene, and carbon (containing BES buffer, Clerol® antifoaming agent (Henkel-Nopco, Leeds, UK), and alginate binder), were screen-printed at a coating thickness of about 20 µm over a portion of the conducting layer of carbon. A Sericard® insulating layer (approximately 20 µm thick) was screen-printed over the entire area of the conducting layer, thereby leaving a small area of the conducting layer near one of the ends of the major surface of the insulating substrate exposed to function as an electrical contact. A layer of a mixture of silver and silver chloride (approximately 20 µm thick) was printed over the insulating layer to form a second conducting layer. A second Sericard® insulating layer (approximately 20 µm thick) was printed over the conducting layer of silver/silver chloride such that a portion of the silver/silver chloride layer was allowed to remain exposed to function as an electrical contact. The exposed portions of the two conducting layers were used for the removable connection of the electrochemical cell to a measuring device. The measuring device was a homemade potentiostat capable of applying a potential to an electrochemical cell and measuring the current produced. Such a device can be readily adapted from a commercially available potentiostat by one of ordinary skill in the art. A cylindrical passage having a diameter of 3 mm was formed by means of a mechanical punch at the area where the reagents were deposited, such that the diameter of the passage was smaller than the area on which the reagents were deposited. The conducting layer of carbon bearing the layer of reagents formed the working electrode and conducting layer containing silver/silver chloride formed the dual-purpose reference/counter electrode of the electrochemical cell.

EXAMPLE 2

This example illustrates a multi-layer electrochemical cell for the determination of glucose. The conducting layers were formed on both major surfaces of an insulating substrate. A conducting layer comprising a mixture of carbon, glucose oxidase, and ferrocene was applied to a first major surface of a Melinex® insulating substrate by means of screen-printing so as to substantially cover the surface of the Melinex® insulating substrate, while leaving a portion on one of the ends of the first major surface of the Melinex® insulating substrate exposed to form an electrical contact area to allow removable connection to a measuring device. An insulating layer was then applied over the conducting layer by means of screen-printing in such a manner as to leave an area adjacent to the exposed portion of the insulating substrate exposed to form an electrical contact area to allow removable connection to a measuring device. A layer comprising a mixture of silver and silver chloride was then applied to the second major surface of the Melinex® insulating substrate by means of screen-printing in a pattern similar to that of the conducting layer comprising carbon. The portion of the major surface of the insulating substrate directly opposite to the contact area was not covered by the layer containing the mixture of silver and silver chloride. The insulating layer was applied by means of screen-printing onto the layer containing silver/silver chloride in such a manner as to allow the area adjacent to area printed area and opposite to the area not printed on the conducting layer to remain exposed. This exposed area allows the electrochemical cell to make electrical contact with the measuring device when inserted to the measuring device. A passage was formed in the electrochemical cell assembly by punching a hole having a diameter of 4 mm through all layers by means of a mechanical punch. The portion of the conducting layers thus exposed to the passage formed the electrodes of the electrochemical cell.

The dimensions of the components in the electrochemical cell of this example were substantially similar to those of the electrochemical cell described in Example 1.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An electrochemical cell comprising:
   an insulating substrate having a plurality of layers thereon, said layers comprising:
   at least two conducting layers, wherein one of said conducting layers is a working electrode, said working electrode in contact with at least one reagent, wherein said at least one reagent comprises an enzyme;
   and at least two insulating layers, wherein said insulating substrate or at least one of said at least two insulating layers is interposed between said at least two conducting layers, wherein each major surface of each conducting layer is in contact with a major surface of said insulting substrate or a major surface of at least one of said at least two insulating layers; and a substantially uniform passage extending from a first outer side of the electrochemical cell to a second outer side of the electrochemical cell opposite the first outer side, the passage being formed through each of said at least two conducting layers and each of said at least two insulating layers to expose edges of each of said at least two conducting layers and each of said at least two insulating layers, said edges collectively forming a wall or walls of said passage, said exposed edges of said at least two conducting layers forming said working electrode and a second electrode of said electrochemical cell, the passage capable of receiving a liquid sample.

2. The electrochemical cell of claim 1, wherein said electrochemical cell comprises two conducting layers and two insulating layers.

3. The electrochemical cell of claim 2, further including a third conducting layer and a third insulating layer.

4. The electrochemical cell of claim 1, further including a second working electrode.

5. The electrochemical cell of claim 4, wherein said working electrodes are capable of determining the presence of, or the concentration of, the same analyte.

6. The electrochemical cell of claim 4, wherein said working electrodes are capable of determining the presence of, or the concentration of, different analytes.

7. The electrochemical cell of claim 1, wherein one of said at least two conducting layers is a counter electrode.

8. The electrochemical cell of claim 1, wherein one of said at least two conducting layers is a reference electrode.

9. The electrochemical cell of claim 1, wherein one of said at least two conducting layers is a dual-purpose reference/counter electrode.

10. The electrochemical cell of claim 1, said at least one passage has a volume not exceeding 1 microliter.

11. The electrochemical cell of claim 1, wherein said passage has a regular shape.

12. The electrochemical cell of claim 1, wherein said passage has an irregular shape.

13. The electrochemical cell of claim 1, wherein said at least one reagent is integral with said working electrode.

14. The electrochemical cell of claim 1, wherein the thickness of each conducting layer does not exceed 100 micrometers.

15. The electrochemical cell of claim 1, wherein the thickness of each insulating layer does not exceed 100 micrometers.

16. The electrochemical cell of claim 1, wherein said insulating substrate is interposed between two conducting layers.

17. The electrochemical cell of claim 1, wherein said at least one insulating layer is interposed between two conducting layers.

18. The electrochemical cell of claim 1, wherein a passage is formed through said insulating substrate.

* * * * *